(12) United States Patent
Trösch et al.

(10) Patent No.: US 6,509,188 B1
(45) Date of Patent: Jan. 21, 2003

(54) PHOTOBIOREACTOR WITH IMPROVED SUPPLY OF LIGHT BY SURFACE ENLARGEMENT, WAVELENGTH SHIFTER BARS OR LIGHT TRANSPORT

(75) Inventors: Walter Trösch, Stuttgart (DE); Ulrike Schmid-Staiger, Neckartenzlingen (DE); Armin Zastrow, Freiburg (DE); Alexander Retze, Freiburg (DE); Franz Brucker, Freiburg (DE)

(73) Assignee: Fraunhofer-Gesellschaft Zur (DE)

( * ) Notice: Subject to any disclaimer, the term of this patent is extended or adjusted under 35 U.S.C. 154(b) by 0 days.

(21) Appl. No.: 09/926,278
(22) PCT Filed: Apr. 6, 2000
(86) PCT No.: PCT/EP00/03089
§ 371 (c)(1), (2), (4) Date: Oct. 31, 2001
(87) PCT Pub. No.: WO00/61719
PCT Pub. Date: Oct. 19, 2000

(30) Foreign Application Priority Data

Apr. 13, 1999 (DE) .......................... 199 16 597

(51) Int. Cl.[7] ................................. C12M 1/00
(52) U.S. Cl. .................... 435/292.1; 435/420; 47/59 R; 47/58.1 LS; 47/DIG. 6
(58) Field of Search .............................. 435/420, 292.1, 435/295.1, 295.2; 47/59 R, 58.1 LS, DIG. 6

(56) References Cited

U.S. PATENT DOCUMENTS

| 3,959,923 A | 6/1976 | Selke |
| 4,473,970 A | 10/1984 | Hills .............................. 47/14 |
| 4,952,511 A | 8/1990 | Radmer ...................... 435/314 |
| 5,151,347 A | 9/1992 | Delente et al. ................. 435/3 |
| 5,162,051 A | 11/1992 | Hoeksema .................... 47/1.4 |

FOREIGN PATENT DOCUMENTS

| DE | 4440081 | | 5/1996 |
| DE | 19611855 | | 8/1997 |
| DE | 19644992 | | 3/1998 |
| DE | 19746343 | | 4/1999 |
| GB | 2235210 | * | 2/1991 |
| JP | 4-91781 | | 3/1992 |
| WO | 91/08314 | | 6/1991 |
| WO | WO01/74990 | * | 10/2001 |

* cited by examiner

Primary Examiner—David A. Redding
(74) Attorney, Agent, or Firm—Piper Rudnick, LLP; Steven B. Kelber (57) ABSTRACT

A photobioreactor is described that has a reactor chamber that is made of light-transparent material and that has an increased surface area.

36 Claims, 5 Drawing Sheets

AIRLIFT LOOP REACTOR – BASIC TYPE OF PHOTOBIOREACTOR

3D VIEW

LONGITUDINAL SECTION

PLAN VIEW

FIG.4

GROWTH RATE AND PRODUCTIVITY OF CHLORELLA VULAGARIS AS A FUNCTION OF CELL CONCENTRATION IN REACTORS WITH AND WITHOUT LATERAL RECESSES (VIGREUX COLUMN AND FLAT TUBE)

FIG.5

PHOTOBIOREACTOR WITH IMPROVED SUPPLY OF LIGHT BY SURFACE ENLARGEMENT, WAVELENGTH SHIFTER BARS OR LIGHT TRANSPORT

The invention relates to a novel photobioreactor for producing biomass.

Photobioreactors are fermenters in which phototrophic microorganisms, such as algae, cyanobacteria and purple bacteria are cultivated, that is to say in which either the growth and the propagation of these cells is made possible or the production of various substances is promoted by means of phototrophic cells.

Such photobioreactors are described, for example, in the following publications:

(i) "Biomass and Icosapentaenoic Acid Productivities from an Outdoor Batch Culture of *Phaeodactylum tricornutum* UTEX 640 in an Airlift Tubular Photobioreactor", Appl. Microbiol. Biotechnol. (1995), 42, pp. 658–663, (ii) "Autotrophic Growth and Carotenoid Production of *Haematococcus pluvialis* in a 30 Liter Air-Lift Photobioreactor", Journal of Fermentation and Bioengineering (1996), Vol. 82, No. 2, pp. 113—118, (iii) "Light Energy Supply in Plate-Type and Light Diffusing Optical Fiber Bioreactors", Journal of Applied Phycology (1995), 7, pp. 145–149, (iv) "A Simplified Monodimensional Approach for Modeling Coupling between Radiant Light Transfer and Growth Kinetics in Photobioreactors", Chemical Engineering Science (1995), Vol. 50, No. 9, pp. 1489–1500.

A principle field of application of photobioreactors is the production of microalgae, which have a share of 30% of the primary production of biomass generated worldwide. In this connection, they are the most important $CO_2$ consumers. Microalgae are therefore capable of having an environmental load reduction effect if they are used for regenerative substance production. Substances that are produced in this way then contribute to the reduction of $CO_2$ emission into the atmosphere since they replace fossil-produced substances.

The microalgae include, on the one hand, the procaryotic cyanobacteria as well as eucaryotic microscopic algae classes. These organisms supply a wide variety of substance classes that can be used for pharmaceutical, cosmetic, nutritional and animal nutrition purposes and for technical purposes (for example, heavy-metal adsorption). Important substance classes in this connection are lipophilic compounds, such as, for example, fatty acids, lipids, sterols and carotenoids, hydrophilic substances such as polysaccharides, proteins or amino acids and phycobilin proteins (pigments), and also the total biomass as protein-rich raw material low in nucleic acid.

BRIEF DESCRIPTION OF THE DRAWINGS

FIG. 1 shows the cross section of various photobioreactors having increased surface areas wherein.

In the Federal Republic of Germany, as also on an international scale, there is an increasing trend to replace synthetic active ingredients by using natural substances having equivalent or improved application properties. Of increasing interest are antioxidant active ingredient complexes and polyunsaturated fatty acids having therapeutic potency in the field of cosmetics, medicine and the health food market. These attractive antioxidants include the tocopherols (vitamin E) and carotenoids, such as β-carotene and astaxanthin.

The cost effectiveness of the substances produced by microalgae is primarily determined by the productivity of the selected algae species. But only if, at the same time, a high efficiency of conversion of solar radiation energy into the desired biomass form is achieved and the energy consumption and the costs of production, installation and plant operation are kept extremely low. High biomass productivity is a problem of optimum light distribution per unit volume. The absorption of light by algae results in a severe decrease in light with increasing layer thickness and, at the same time, a mutual self-shadowing takes place. This phenomenon results in a theoretical layer formation in the reactor:

(1) an outer algae layer that is exposed to high light intensities that may result in photo inhibition, (2) a central layer having ideal illumination, (3) an inner algae layer having a light deficiency and a high respiration rate.

The object of the invention is therefore to provide a photobioreactor in which the solar radiation available is coupled in and can be distributed in such a way that all the microorganisms have an equally high photosynthesis activity regardless of position.

The invention relates to a photobioreactor that has a reactor chamber having an increase in surface area that is greater than the planar enveloping surface of a volume.

Said increase in surface area results in a better spatial distribution of the light over the reactor cross section and consequently in an optimization of the light intensity in the entire reactor compared with the photobioreactors known in the prior art. The reactor chamber of the latter normally comprises pipes or so-called "tubes". Their cross section is circular. In addition, photobioreactors are known that have reactor chambers whose cross section is rectangular. Such a cross section has more area as a volume envelope than the circular cross section of a pipe. This is shown diagrammatically in FIG. 1.

Figure 1:
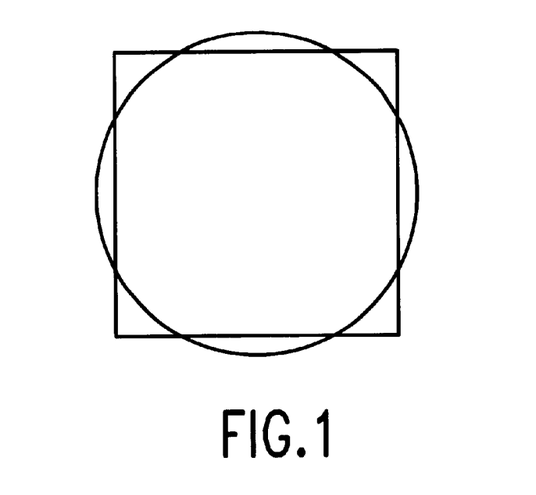
Figure 1A:
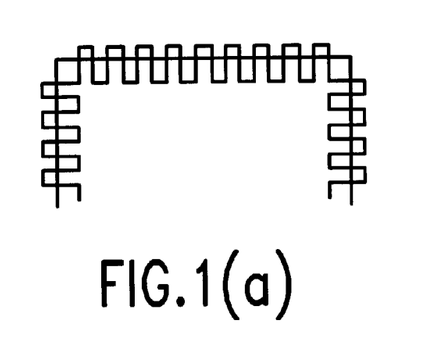
FIG. 1*a* shows a meander shaped reactor surface.
Figure 1B:
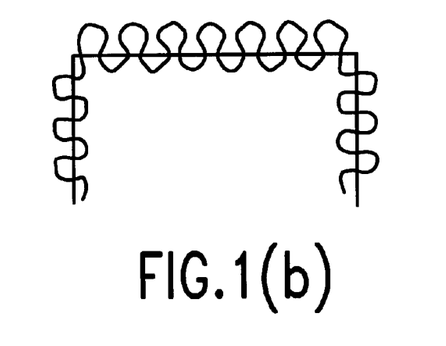
FIG. 1*b* shows a sinusoidal reactor surface and FIG. 1*c* shows a reactor having light transparent webs.
Figure 1C:
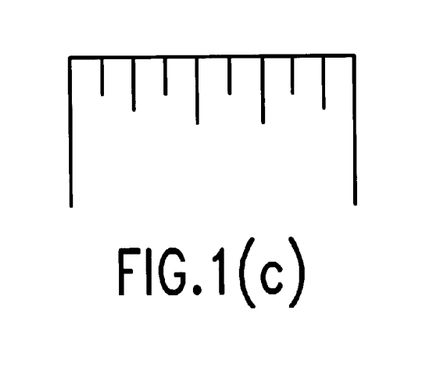
Figure 4:
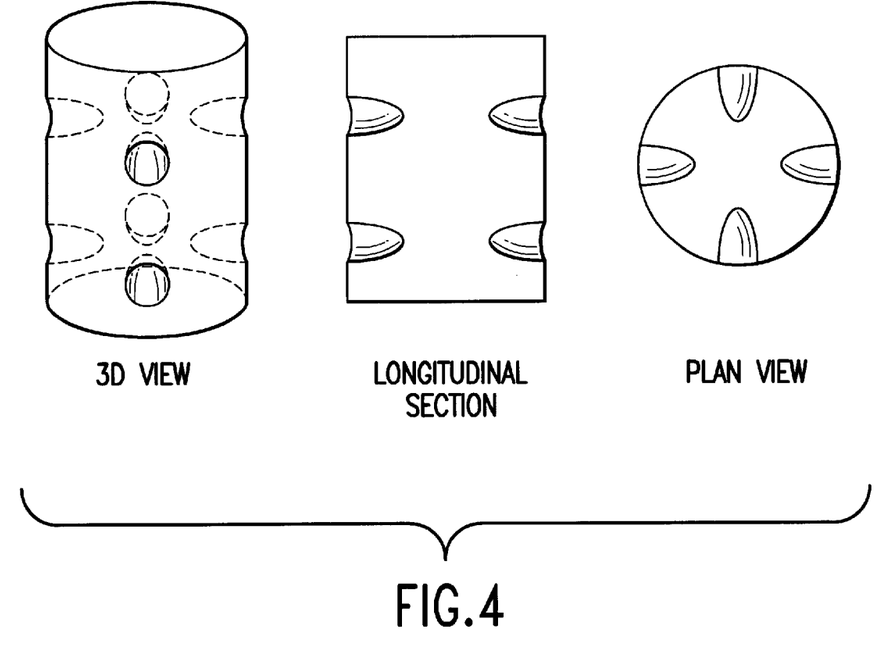
FIG. 4 shows a tube reactor having recesses according to the invention.

The photobioreactor according to the invention has an increase in surface area compared with the above mentioned known reactor geometries, as is shown by way of example in FIG. 1. Here, (a) denotes a meander-shaped and (b) a sinusoidal reactor surface. (c) denotes a reactor geometry having light-transparent webs. A further embodiment is shown in FIG. 4 in which glass extensions inwards represent the increase in surface area.

Common to all these geometries is the fact that the reactor surface area is increased compared with known geometries.

In the photobioreactor according to the invention, all the reactor chamber geometries can in principle be used that have an increase in surface area compared with the planar envelope (square or rectangular in cross section).

The reactor chamber of the photobioreactor according to the invention is composed of a light-transparent material, preferably glass or plexiglass.

In accordance with a further embodiment of the invention, the surface-area-increasing geometry of the reactor chamber is achieved by a glass tube into whose interior glass extensions project. Said glass extensions are mounted perpendicularly or at an angle on the internal surface in an alternating manner.

At the same time, the glass extensions increase the turbulence in the liquid phase. Instead of glass, it is also possible to use another light-transparent material, such as, for example, plexiglass.

Increasing the turbulence achieves the so-called "flashing-light effect". The flashing-light effect means that a high light intensity at short intervals (>1 Hz) is sufficient for a maximum photosynthesis activity. This can be achieved by a turbulent flow conduction in the reactor that exposes the cells at short intervals to high light intensities at the reactor surface and they can therefore process the light energy collected in the subsequent dark phases.

The invention therefore relates, furthermore, to a photobioreactor whose reactor chamber has, in addition to an increased surface area, devices for producing a turbulent flow conduction.

As already mentioned, said turbulence can be achieved by a surface-area-increasing geometry of the reactor chamber, in particular by glass extensions that are situated on the interior wall of the reactor chamber. A turbulent flow conduction may also be achieved, furthermore, by installing static mixers (baffles). Like the abovementioned glass extensions, these internals can, in addition, conduct light additionally into the reactor. A further way of generating turbulence in the photobioreactor according to the invention is to provide an gassing device that achieves the desired effect at an appropriate gassing rate. The provision of flow-conducting internals can also improve the flashing-light effect if a defined frequency is established for the illumination time.

The intense mixing with as much turbulence as possible results in a light distribution by bringing the algae to the light. This can control the frequency and the duration of the "illumination phases" in a defined manner.

The energy density in the reactor chamber of the photobioreactor according to the invention may, furthermore, be increased by using so-called wavelength shifters. The wavelength shifter converts the component of the light not absorbed by phototrophic microorganisms in such a way that as large a component of the light as possible or the totality of the radiation is displaced into that frequency band that can be absorbed by the photocentre of phototrophic microorganism used. Consequently, the holometric radiation density is specifically increased in such a way that the productivity is substantially increased per unit reactor volume compared with bioreactors irradiated with normal light.

In this case, the wavelength shifter may be disposed between a reflector and the actual reactor chamber. The wavelength shifter may, however, also be provided between the light source and the reactor chamber, with the result that the reflector can be omitted.

Omnission of the reflector is likewise possible if the wavelength shifter is in the form of rods, plates, fibres or particles in the reactor chamber. Furthermore, the wavelength shifter can also be a coating directly on the reactor wall on the outside or inside of the reactor chamber.

Substances that are capable of displacing the wavelength are known per se to the person skilled in the art and are described, for example, in the following publications:

E. Locci et al., "Test of a Lead-Plexipop Calorimeter Module Viewed by Wave Length Shifter Bars", Nucl. Instrum. Methods 164, (1979), pp. 97–104, S. W. Han et al., "Radiation Hardness Tests of Scintillating Tile/WLS Fiber Calorimeter Modules", Nucl. Instrum. Methods A365 (1995), pp. 327–351.

The wavelength shifters used in the photobioreactor according to the invention preferably comprise fluorescent substances. Such fluorescent substances are substances that, after absorption of light, radiate light again, the energy for the radiated light not being essentially drawn from the heat content of the fluorescent substance, but originating from the excitation energy supplied by the absorbed light.

The fluorescent substance may be contained in a carrier, such as an organic or inorganic glass.

For example, organic fluorescent substances may be contained in organic glasses, such as acrylic glass polycarbonate or acrylic glass polystyrene. Ions of rare earths, which can likewise be used as fluorescent substances, are preferably contained in inorganic glasses. Solutions of the fluorescent substances in transparent solvents can also be used as wavelength shifters.

The fluorescent substances have the property of absorbing light and reemitting it, in general after a very short time (frequently only a few nsec). It is important that this reemission of the light occurs virtually without loss in some substances, i.e. the fluorescent quantum yield (number of emitted photons divided by the number of absorbed photons) is >90%, often close to 100%. It is furthermore of importance that the fluorescent spectrum is displaced towards longer wavelengths compared with the absorption spectrum, i.e. a dyestuff converts UV and violet light into blue light, or another blue light into green light, etc. As a result of combining a plurality of dyestuffs, either in the same plate or, for example, by layers behind one another of differently coloured plates, a larger wavelength range can also be leapt over in one step, for instance blue light can be converted directly into red light.

Expected of a wavelength shifter is high fluorescent quantum yield, good solubility in the carrier material provided (in order to be able to achieve sufficiently high light absorption), an optimum position of absorption spectrum and emission spectrum for the particular application and a sufficiently long-term stability under the conditions of use envisaged. Typical examples of the use of wavelength shifters are whiteners in detergents, UV-absorbing dyestuffs that emit blue to mask the yellowing of washing, and the dyestuffs that are used in scintillation counters to shift shortwave Čerenkov radiation or scintillation radiation to a wavelength range that is optimum for the spectrosensitivity of the photodetectors used.

Preferred examples of organic fluorescent substances that can be used as wavelength shifters in the photobioreactor according to the invention are the following naphthalimides and perylene derivatives:

4, 5-dimethoxy-N-(2-ethyl-hexy)naphthalimide, 3,9-Di(i-butoxycarbonyl)-4,10-dicyanoperylene, N,N'-bis(2,6-diisopropylphenyl)perylene-3,4:9,10-tetracarboxylic diimide or N,N'-bis(2,6-diisopropylphenyl)-1,6,7,12-tetraphenoxyperylene-3,4:9,10-tetracarboxylic diimide.

These fluorescent substances all have a very high quantum yield. The maximum absorbances are many 10,000 l/mol·cm.

The fluorescent substances may be present in the carrier material in a concentration of $10^{-7}$ to $10^{-2}$ mol/l. The carrier material preferably then has a thickness of 0.1 to 10 mm.

The use of a wavelength shifter in combination with the better spatial distribution of light over the reactor cross section by establishing an appropriate surface area/volume ratio and the increase in turbulence to achieve a flashing-light effect distribute the light optimally in the reactor chamber of the photobioreactor according to the invention.

Figure 2:
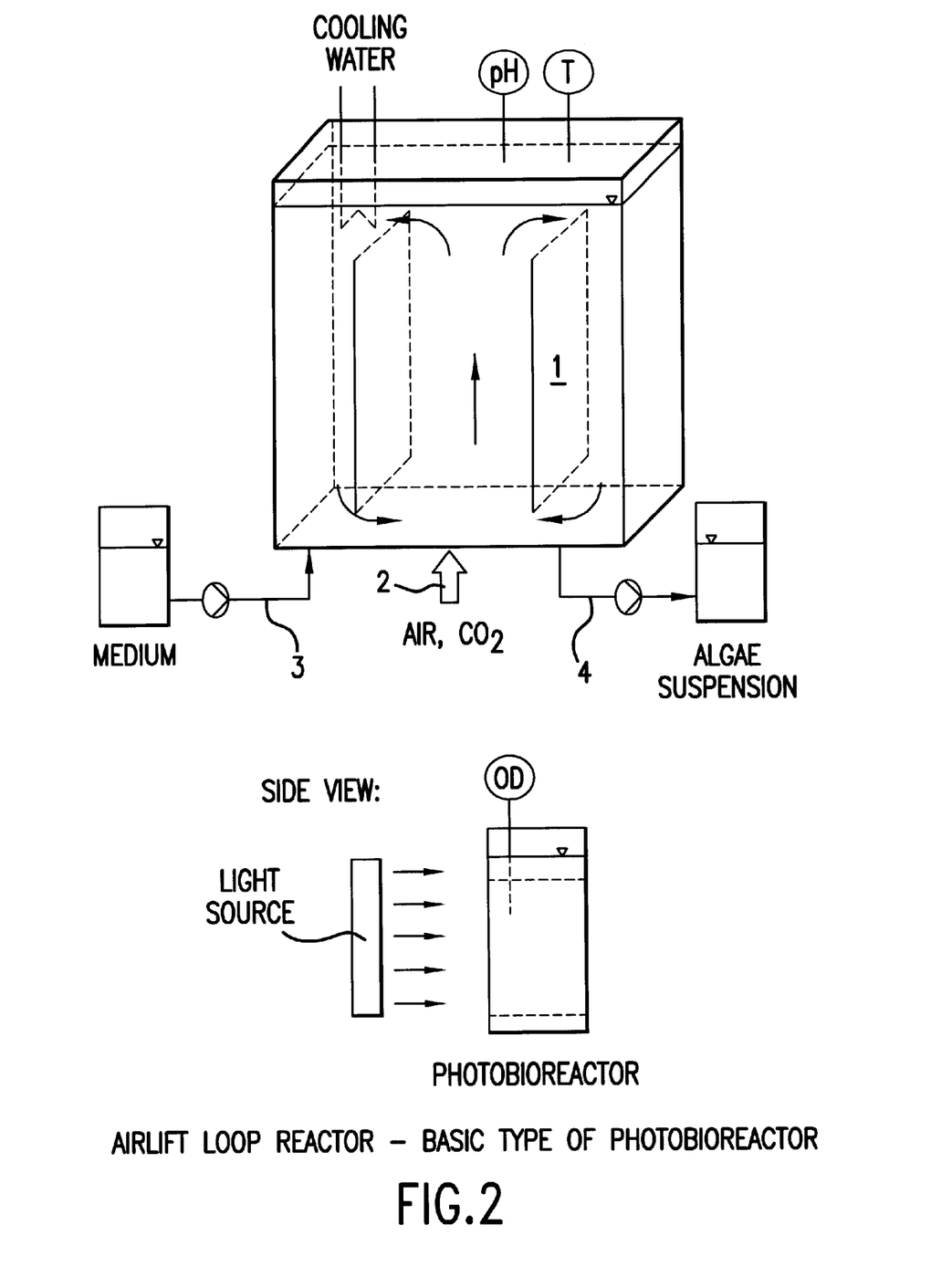
FIG. 2 shows a photobioreactor according to the invention which employs the basic principle of an airlift loop reactor.

FIG. 2 shows the structure of the photobioreactor according to the invention employing the basic principle of an airlift loop reactor. The reactor has a rectangular cross section and two internal surfaces (1) that extend parallel to the reactor chamber walls, devices for injecting air (2) at the lower side of the reactor chamber and devices for supplying (3) a medium and for removing (4) the biomass produced in the reactor chamber.

The internal surfaces serve at the same time as a guide tube.

Plexiglass, for example, which has a high light transparency, can be used as material.

The thorough mixing takes place as a result of injection of air at the lower side of the reactor, with the result that the liquid flows upwards and back down again at the side. The gas exchange and the temperature control take place in the highly turbulent headspace. The temperature control in the headspace eliminates an additional plexiglass wall that would be necessary in the case of a cooling jacket.

The rectangular basic structure and the small reactor depth result in a large surface area/volume ratio and, consequently, the possibility of a high light input into the reactor. The reactor does not have unilluminated zones, with the result that sufficient light can continuously be provided for the cells.

Operation as an airlift loop ensures a high turbulence with low shearing forces acting on the algae cells. Given high turbulence and, at the same time, high radiation intensity, the flashing-light effect can be utilized, according to which the cells do not have to be continuously illuminated. The turbulence can be increased either by the gassing rate or by the installation of static mixers (baffles).

A flow conduction with high turbulence results in a horizontal mixing in addition to vertical mixing. This subjects the phototrophic microorganisms to an interrupted light provision. The cycle time that a phototrophic microorganism spends in the light and then in the dark should be >1 Hz. The turbulence determines the time the microorganisms need in order to be transported back into the illuminated zone again from the unilluminated zone. The length of the transport path is determined by the layer thickness of the reactor (reactor depth).

The installation of flow-conducting elements increases the turbulence and, consequently, the frequency of the transport of the microorganisms from the unilluminated zone into the illuminated zone again can be improved.

In addition, like the recesses in the Vigreux column, said flow-conducting elements could additionally conduct light into the reactor.

The thorough mixing and constant gas flow in the reactor ensure a good introduction of $CO_2$ and discharge of $O_2$.

The simple geometry and the arrangement of the degassing zone in this system make simple scaling-up possible.

Instead of a reactor employing the airlift loop principle, the reactor may also be designed as a plate-fin column.

Figure 3:
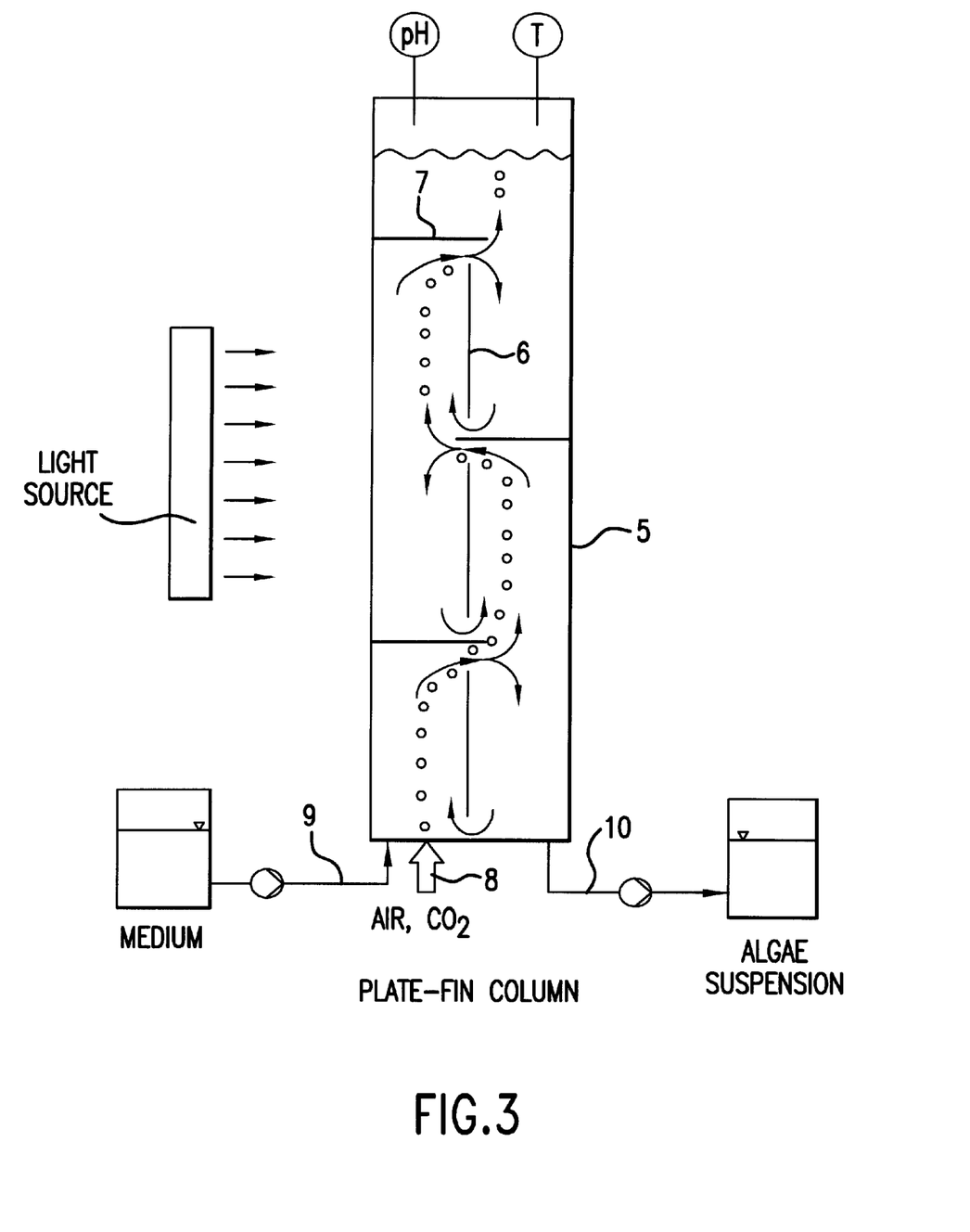
FIG. 3 shows a plate fin column photobioreactor according to the invention.

Such a plate-fin column is shown diagrammatically in FIG. 3. In the latter, (5) denotes a reactor chamber having a rectangular cross section that has internal walls (6, 7) extending parallel (6) and at a right angle (7) to the reactor walls (5).

The plate-fin column has, furthermore, devices for injecting air at the lower side (8) of the reactor chamber, and devices for supplying a medium (9) and for removing the biomass (10) produced in the reactor chamber.

The internal surfaces (6, 7) serve to generate a turbulent flow. Mixing takes place as a result of injection of air at the lower side of the reactor, with the result that the liquid first flows upwards and then back down again at the side. The transverse walls (7) deflect the gas bubbles and result in a flow and vortex formation in the next cell. Gas exchange takes place in the headspace. As a result of the vortex formation in the individual cells, an intensive mixing takes place over the reactor cross section.

The airlift loop reactors described above can also be disposed alongside one another in series, in which case they are connected to one another on the fluid side by the principle of communicating tubes.

The bioreactor according to the invention may also be designed in such a way that it has a plurality of airlift loop reactors that are disposed above one another as plate-fin column.

Finally, FIG. 4 shows diagrammatically the structure of a reactor chamber that is designed as a glass tube into whose interior glass extensions project.

The invention is explained in greater detail by the exemplary embodiment below.

EXEMPLARY EMBODIMENT

A tube reactor was extended by the recesses shown in FIG. 4. Said recesses have a double function in that they both increase the reactor surface area and influence the flow. Vigreux columns are constructed on this principle (likewise for reasons of increase in surface area) and were used directly for comparison tests. A tube reactor having the same geometry without lateral recesses was used as a control. The illumination took place by means of 2 halogen radiators, with the result that 520 $\mu E/(m^2 \cdot s)$ of light was available from one side. The radiated light intensity per unit volume and time was, however, 10% lower in the control reactor than in the Vigreux column.

TABLE

Comparison of the productivity of Chlorella vulgaris in reactors without and with lateral recesses (smooth tube and Vigreux column)

| | Dry weight DW (g/l) | Growth rate $\mu$ (l/h) | Productivity P (mg/l*h) | Change in productivity (%) |
|---|---|---|---|---|
| Smooth tube | 2 | 0.016 | 32 | |
| | 4 | 0.0058 | 23.2 | |
| | 5 | 0.003 | 15 | |
| Vigreux column Experiment 1 (V1) | 2 | 0.01 | 20 | −38 |
| | 4 | 0.0082 | 32.8 | 41 |
| | 5 | 0.006 | 30 | 100 |
| Vigreux column Experiment 2 (V2) | 2 | 0.013 | 26 | −19 |
| | 4 | 0.007 | 28 | 21 |
| | 5 | 0.004 | 20 | 33 |

Figure 5:
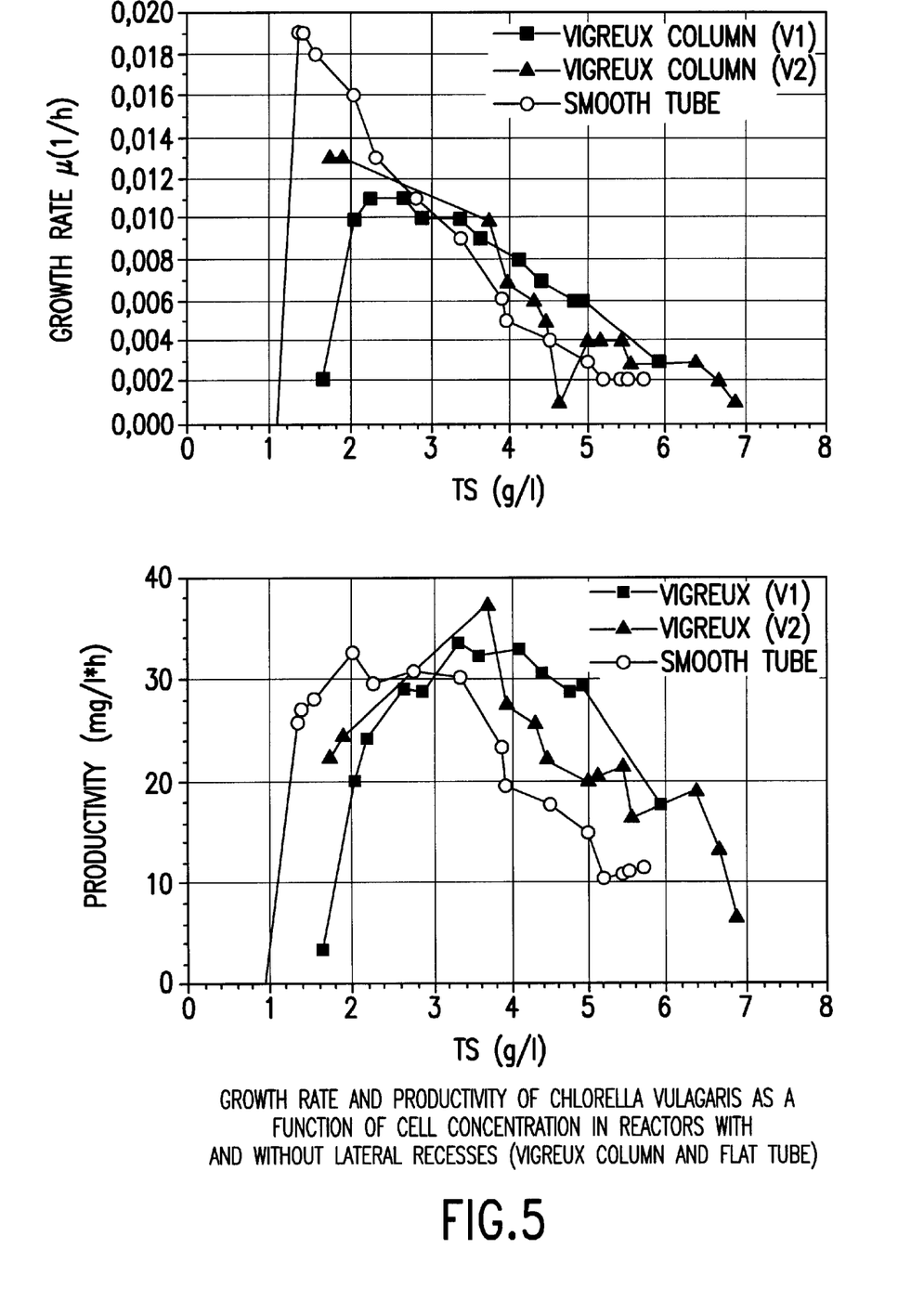
FIG. 5 are graphs showing growth rate and productivity of *Chlorella vulgaris* as a function of cell concentration in reactors with and without lateral recesses.

Direct comparison revealed a 20 to 40% higher productivity in the Vigreux column with 4 g of DW/l and 30 to 100% higher productivity with 5 g of DW/l (cf. FIG. 5) in the Vigreux column compared with the reactor without lateral recesses. (The different results in V1 and V2 are the result of a different preliminary adaptation of the algae cells to the light.)

This shows that an increase in surface area that simultaneously also increases the turbulence can markedly increase the biomass productivity in the case of intensities above the saturation range.

What is claimed is:

1. A photobioreactor comprising a reactor chamber having sidewalls made of light-transparent material defining an interior volume, wherein the reactor chamber has an increase in surface area greater than the planar enveloping surface of the interior volume of the reactor chamber.

2. A photobioreactor according to claim 1, wherein the reactor chamber further comprises devices for producing a turbulent flow conduction.

3. A photobioreactor according to claim 1, further comprising elements that conduct light into the reactor chamber from the outside.

4. A photobioreactor according to claim 1, wherein one or more sidewalls of the reactor have a meander-shaped or sinusoidal cross-section.

5. A photobioreactor comprising a reactor chamber having sidewalls made of light-transparent material defining an interior volume, wherein the reactor chamber further comprises light-transparent webs projecting into the interior of the reactor chamber.

6. A photobioreactor according to claim 1, wherein the reactor chamber comprises a glass tube comprising glass extensions projecting into the interior of the reactor chamber.

7. A photobioreactor according to claim 1, wherein the reactor chamber is an airlift loop reactor or a plate-fin column.

8. A photobioreactor according to claim 7, wherein the reactor chamber has a rectangular cross-section, internal surfaces extending parallel to the reactor chamber sidewalls, air injectors at a lower side of the reactor chamber, and a medium supply tank and a biomass reservoir in fluid communication with the interior of the reactor.

9. A photobioreactor according to claim 7, comprising a plurality of airlift loop reactors connected in series, wherein the interior of each reactor is in fluid communication with an adjacent reactor.

10. A photobioreactor according to claim 7, comprising a plurality of airlift loop reactors arranged vertically to form a plate-fin column.

11. A photobioreactor according to claim 1, further comprising a wavelength shifting compound.

12. A photobioreactor comprising at least one reactor chamber having sidewalls made of light-transparent material, wherein the reactor chamber comprises a first internal surface having first and second opposed edges, wherein the first and second opposed edges of the first internal surface are each spaced from an interior surface of the reactor chamber.

13. The photobioreactor of claim 12, further comprising:
   at least one injector;
   a medium supply tank; and
   a biomass reservoir;
   wherein the at least one injector, the medium supply tank and the biomass reservoir are in fluid communication with the interior of the reactor chamber.

14. The photobioreactor of claim 12, wherein the photobioreactor comprises a plurality of reactor chambers, and wherein the interior of each reactor chamber is in fluid communication with the interior of at least one other reactor chamber.

15. The photobioreactor of claim 14, wherein the reactor chambers are arranged vertically to form a column having a bottom reactor chamber, wherein an upper surface of the bottom reactor chamber forms a lower surface of an adjacent reactor chamber.

16. The photobioreactor of claim 14, wherein the reactor chambers are connected together with pipes or tubes.

17. The photobioreactor of claim 12, wherein the photobioreactor further comprises a wavelength shifting compound incorporated into a surface of the reactor or coated onto a reactor sidewall.

18. The photobioreactor of claim 17, wherein the wavelength shifting compound is selected from the group consisting of 4,5-dimethoxy-N-(2-ethyl-hexyl)naphthalamide; 3,9-Di(i-butoxycarbonyl)-4,10-dicyanoperylene; N,N'-bis (2,6-diisopropylphenyl)perylene-3,4:9,10-tetracarboxylic diimide; and N,N'-bis(2,6-diisopropylphenyl)-1,6,7,12-tetraphenoxyperylene-3,4:9,10-tetracarboxylic diimide.

19. The photobioreactor of claim 12, wherein the reactor chamber further comprises a second internal surface spaced from the first internal surface, the second internal surface having first and second opposed edges, wherein the first and second opposed edges of the second internal surface are each spaced from an interior surface of the reactor chamber.

20. The photobioreactor of claim 12, wherein the reactor chamber has a rectangular cross-section.

21. A method of cultivating phototropic microorganisms in a reactor as set forth in claim 12, the method comprising:

supplying the reactor with medium comprising phototropic microorganisms;

injecting a gas into the reactor such that medium in the reactor flows upwardly in a first internal region, impinges on an interior surface of the reactor and flows over the first opposed edge of the first internal surface, wherein at least a portion of the medium flowing over the first opposed edge flows downwardly in a second internal region, impinges on an interior surface of the reactor, and flows over the second opposed edge of the first internal surface to be recirculated into the first internal region;

impinging light from a light source onto the reactor; and removing biomass produced in the reactor chamber.

22. The method of claim 21, wherein the light impinges on a wavelength shifting substance.

23. The method of claim 22, wherein the wavelength shifting substance comprises a fluorescent compound selected from the group consisting of 4,5-dimethoxy-N-(2-ethyl-hexyl)naphthalamide; 3,9-Di(i-butoxycarbonyl)-4,10-dicyanoperylene; N,N'-bis(2,6-diisopropylphenyl)perylene-3,4:9,10-tetracarboxylic diimide; and N,N'-bis(2,6-diisopropylphenyl)-1,6,7,12-tetraphenoxyperylene-3,4:9,10-tetracarboxylic diimide.

24. The method of claim 21, wherein the medium flows turbulently through the reactor.

25. A method of cultivating phototropic microorganisms in a reactor as set forth in claim 19, the method comprising:

supplying the reactor with medium comprising phototropic microorganisms;

injecting a gas into the reactor such that medium in the reactor flows upwardly in a first internal region between the first and second internal surfaces, impinges on an interior surface of the reactor and flows over the first and second internal surfaces, wherein medium flowing over the first opposed edge of the first and second internal surfaces flows downwardly in second and third internal regions, respectively, impinges on an interior surface of the reactor and flows over the second opposed edge of the first and second inner surfaces, respectively, to be recirculated into the first internal region;

impinging light from a light source onto the reactor; and removing biomass produced in the reactor chamber.

26. The method of claim 25, wherein the light impinges on a wavelength shifting substance.

27. The method of claim 26, wherein the wavelength shifting substance comprises a fluorescent compound selected from the group consisting of 4,5-dimethoxy-N-(2-ethyl-hexyl)naphthalamide; 3,9-Di(i-butoxycarbonyl)-4,10-dicyanoperylene; N,N'-bis(2,6-diisopropylphenyl)perylene-3,4:9,10-tetracarboxylic diimide; and N,N'-bis(2,6-diisopropylphenyl)-1,6,7,12-tetraphenoxyperylene-3,4:9,10-tetracarboxylic diimide.

28. The method of claim 25, wherein the medium flows turbulently through the reactor.

29. A photobioreactor comprising a tubular reactor chamber made of light-transparent material, the reactor chamber comprising a plurality of projections extending from the reactor wall into the interior of the reactor chamber.

30. The method of claim 29, wherein the projections are elongate projections having a major dimension oriented perpendicularly to the reactor surface.

31. The method of claim 29, wherein the projections are elongate projections having a major dimension oriented at an angle to the reactor surface.

32. The method of claim 29, wherein the projections are made of light-transparent material.

33. A method of cultivating phototropic microorganisms in a reactor as set forth in claim 29, the method comprising:

flowing medium comprising phototropic microorganisms through the reactor chamber; and impinging light from a light source onto the reactor.

34. The method of claim 33, wherein the light impinges on a wavelength shifting substance.

35. The method of claim 34, wherein the wavelength shifting substance comprises a fluorescent compound selected from the group consisting of 4,5-dimethoxy-N-(2-ethyl-hexyl)naphthalamide; 3,9-Di(i-butoxycarbonyl)-4,10-dicyanoperylene; N,N'-bis(2,6-diisopropylphenyl)perylene-3,4:9,10-tetracarboxylic diimide; and N,N'-bis(2,6-diisopropylphenyl)-1,6,7,12-tetraphenoxyperylene-3,4:9,10-tetracarboxylic diimide.

36. The method of claim 33, wherein the medium flows turbulently through the reactor.

* * * * *